United States Patent [19]
Gertzman et al.

[11] Patent Number: 5,460,621
[45] Date of Patent: Oct. 24, 1995

[54] COMPOSITE TISSUE DISPLACEMENT SPONGE

[75] Inventors: Arthur A. Gertzman, Woodbridge; Douglas R. Valentine, Oakdale, both of Conn.

[73] Assignee: Merocel Corporation, Mystic, Conn.

[21] Appl. No.: 205,749

[22] Filed: Mar. 4, 1994

[51] Int. Cl.⁶ ..................................... A61F 13/15
[52] U.S. Cl. .......................... 604/358; 604/369; 604/378; 604/379; 604/385.1; 128/899
[58] Field of Search .................. 604/358, 378, 604/379, 382, 389, 397, 290, 304, 362, 585.1, 369; 401/200, 196; 15/244.3; 215/11.1, 11.4; 430/505; 264/41; 128/844, 918, 898, 899; 602/42

[56] References Cited

U.S. PATENT DOCUMENTS

| | | | |
|---|---|---|---|
| 3,961,629 | 6/1976 | Richter et al. | 128/296 |
| 4,019,498 | 4/1977 | Hawtrey et al. | 128/1 R |
| 4,034,759 | 7/1977 | Haerr | 128/260 |
| 4,098,728 | 7/1978 | Rosenblatt | 521/141 |
| 4,159,719 | 7/1979 | Haerr | 128/260 |
| 4,327,728 | 5/1982 | Elias | 128/285 |
| 4,533,356 | 8/1985 | Bengmark et al. | 604/358 |
| 4,553,966 | 11/1985 | Korteweg | 604/317 |
| 4,565,722 | 1/1986 | Highgate et al. | 428/36 |
| 4,889,107 | 12/1989 | Kaufman | 128/20 |
| 4,979,947 | 12/1990 | Berman | 604/369 |
| 5,074,840 | 12/1991 | Yoon | 604/15 |
| 5,149,332 | 9/1992 | Walton et al. | 604/358 |
| 5,387,206 | 2/1995 | Valentine et al. | 604/358 |

Primary Examiner—Lee S. Cohen
Assistant Examiner—Stephen Huang
Attorney, Agent, or Firm—Gipple & Hale; John S. Hale

[57] ABSTRACT

A tissue/organ retraction or displacement sponge comprising a rigid dry absorbent shaped sponge body constructed of laminated layers of sponge material with differing pore size density causing differing swelling rates and expansion. The sponge when hydrated substantially expands protecting an organ or moving the same to be a different area.

27 Claims, 2 Drawing Sheets

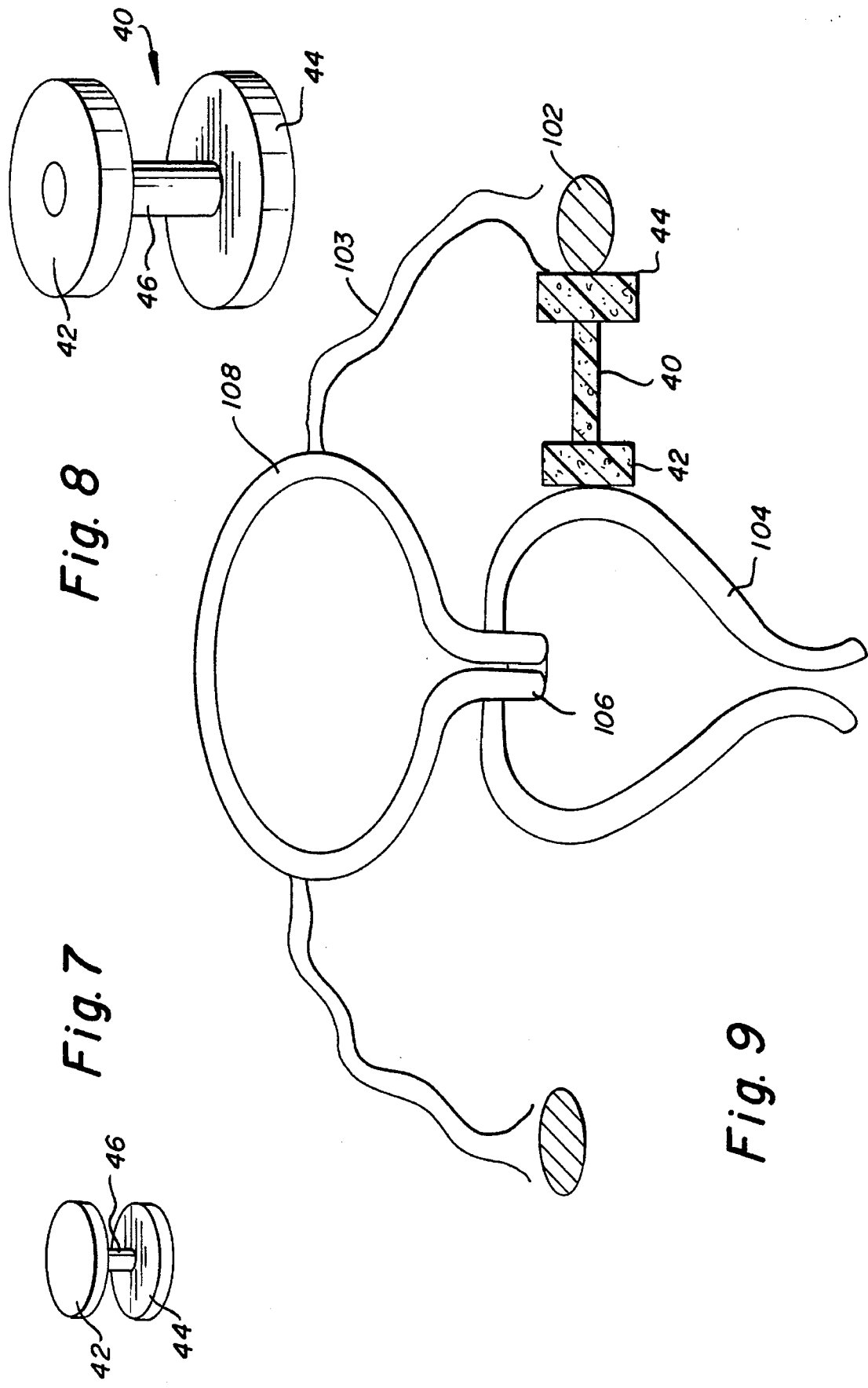

COMPOSITE TISSUE DISPLACEMENT SPONGE

BACKGROUND OF THE INVENTION

The present invention generally relates to securing layers of differing density sponge material together to form a composite body and mechanically treating the composite sponge body so that it will form a specific shape upon hydration.

There currently is a need to provide medical devices which can be inserted into the human body in one condition and when hydrated by body fluids change their shape into a desired shape or form, pushing an organ or tissue to a different position, or providing a protective shield for the organ or tissue to protect the same during surgery or treatment.

It is often necessary during surgery to displace or temporarily relocate tissue or organs from their natural anatomical position. This is done to facilitate surgery at the site. Organs and tissue must be handled gently to prevent damage or to minimize the tendency to produce adhesions, post operatively.

Many devices have been developed to address this problem: tapes, metal retractors of various designs and fabric sponges have all been used. These are all functional but have various deficiencies.

Tapes are useful for displacing small organs such as veins and arteries. They have tendency to cut through the organ when pulled to adjust the position of the organ because of their linear contact with the organ.

Metal or plastic retractors have proven to be useful. They can hold large organs or pedicles of tissue, even when put under considerable tension. However, the metal surface and the high degree of compression within the jaws of the retractor tends to create necrosis of the tissue.

Fabric sponges are also very useful for packing cavities and tissue adjacent to the organ to be protected. They are conformable to the space available, are soft and to some degree absorbent. The fabric sponges suffer from the need to use large quantities of sponge to get sufficient mass to displace tissue and from being weak and easily frayed creating a risk of leaving filaments behind. Such filaments will be treated by the body as foreign matter and could become a nexus for infection or create granuloma.

While medical sponges are generally used to absorb bodily fluids as blood, serum, spinal fluid, tissue fluid, urine, sweat, bile, digestive juices and other fluids, they are also used to displace organs or tissues and dam and hold organs and tissues. See for example U. S. Pat. No. 4,533,356 directed toward an absorbent rod shaped device used to keep organs in a given position; U.S. Pat. No. 4,889,107 directed toward a surgical dam constructed of an open celled plastic foam having a metal core allowing it to be bent into a desired configuration and U.S. Pat. No. 3,961,629; a surgical sponge pad having a surfactant coating to accelerate absorption of body fluids into the sponge pad.

A number of other patents are known which show various devices which have been designed to change shape to provide a desired medical function or to impart a mechanical force for accomplishing a desired result.

In this area, U.S. Pat. No. 5,149,332 discloses an absorbent product which is longitudinally compressed or microcreped to produce microroundulations by compressing the web in its own plane in the direction of its length with compressive forces exerted substantially parallel to a longitudinal direction of the material. The product when compressed has at least 10 microroundulations per inch in the layer in the direction of treatment. The microroundulated layer is shape-retentive and has stored mechanical energy capable under an activating condition such as hydration to cause the product to expand. The product is envisioned to be used as superabsorbent assemblages, menstrual tampons, pads such as bandages, compresses, rolls and the like and liquid distributing articles.

A number of shaped polymeric compositions for surgical use which can absorb liquid and thereby expand or contract in one direction are shown by U.S. Pat. No. 4,565,722. Examples of such different shaped memory devices are shown in the figures of the patent, the even numbers representing expanded devices. One shaped memory device is a triangular shaped endodontic point for insertion into a tooth after a nerve cavity has been removed. The axial length stays unchanged while the product swells radially. Another shaped memory device is initially in the form of a sheath and expands radially for holding severed nerve ends, veins or arteries in close proximity so that the contracted ends of the sheath provide a soft and pliable grip on the nerve, vein or artery ends. Another shaped device is shown which swells in contact with body fluid to a dumbbell shape which can be used for providing a permanent but non-irritant Fallopian tube closure. Still another shaped memory device is directed to a cylindrical blank which expands in diameter. Another shaped memory device expands in thickness only provided that $d_1 d_2$ equals the linear expansion ratio of the material during hydration to give the expanded insert an arcuate outer surface for use as a breast implant.

U.S. Pat. No. 4,159,719 discloses a dehydrated wick of tightly coiled cellular sponge like material which when hydrated uncurls and expands radially to snugly engage the inner peripheral wall of the ear canal. Likewise U.S. Pat. No. 4,034,759 discloses a moisture expandable prosthesis constructed of a hollow cylindrical wick of dehydrated regenerated cellulose sponge material. The sponge material is tightly compressed so that it is rigid for insertion endwise into a body opening. When the wick is moistened, it expands radially to engage the inner peripheral walls of the opening and when used in association with an ear canal, provides an axial opening through which the expanded member permits sound waves to reach the ear U.S. Pat. No. 4,979,947 discloses a resilient foam material collapsed into a small volume condition having a string or cord passing through the material which when introduced into an orifice absorbs moisture to expand at a predetermined size and shape for blockage. Traction on the string during withdrawal results in compression of the contained foam cube allowing comfortable withdrawal from the body orifice.

A multi-layered tampon formed by folding over a single layer of absorbent batt is disclosed by U.S. Patent Number 4,327,728. Pockets containing hydrocolloid and introfying particles are placed so as to lie between the layers and project into each layer. The dry solid granules of hydrocolloid particles when wetted begin to swell expanding the pockets. As the pockets expand, the expanding walls push the adjacent fibers of the batt aside while keeping the hydrocolloid particles trapped within the pockets thus significantly increasing the total absorptive capacity of the structure.

U.S. Pat. No. 4,019,498 discloses a vaginal device for urinary incontinence in the form of a cellular mushroom-shaped body which is precompressed and inserted in a plastic sleeve. After insertion into the vagina the sleeve is pierced allowing the introduction of air into the sponge-like cells of the device permitting it to expand and exert pressure on the urethra.

Because sponge material is difficult to place in human body Cavities after it has absorbed fluid and obtain the desired results and since pre-wetting may decrease the amount of fluid that can be adsorbed, some absorbent sponges and dressings are placed in human body cavities in a dry compressed form. The present invention takes this prior art one step further and provides a layered different density sponge material which when placed in the human body cavity absorbs fluid to expand into another shape due to the different expansion capacities and equilibrium water concentration of the different density sponge materials.

SUMMARY OF THE INVENTION

The present invention is directed towards a layered medical sponge device having composite absorbent layers of different densities. The sponge is compressed into a rigid and dry form and expands when the device is hydrated. The sponge is constructed of layers of polyvinyl acetal, a material with high absorptive properties and immediate wicking. Upon hydration each of the layers of sponge material of differing pore size has a different rate of water absorption and consequently a differing rate of swelling.

It is the purpose of this invention to use the different swelling rates due to different equilibrium water concentration or capacity of PVAc sponges to achieve a compound sponge made of two or more layers of PVAc sponge of different density. The compound sponge with layers of different densities has the surprising property of curling or folding on itself because of the differential in the swelling rates of the two layers. It has been found that the curling or folding property is a permanent feature of the wet sponge as long as it remains wet.

In the accompanying drawings, there is shown an illustrative embodiment of the invention from which these and other objectives, novel features and advantages will be readily apparent.

BRIEF DESCRIPTION OF THE DRAWINGS

FIG. 7 is a perspective view of a disc spacer device embodiment of the invention in a compressed state;

FIG. 8 is a perspective view of the disc spacer device of FIG. 7 in a hydrated expanded state; and FIG. 9 is a schematic view of the disc spacer device of FIG. 7 used to displace an ovary during surgery.

DETAILED DESCRIPTION OF THE DRAWINGS

Figure 1:
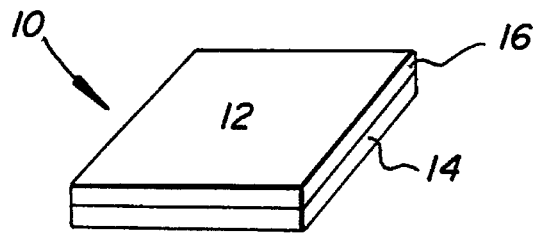
FIG. 1 is a perspective view of the present composite layered material displacement sponge invention.
Figure 2:
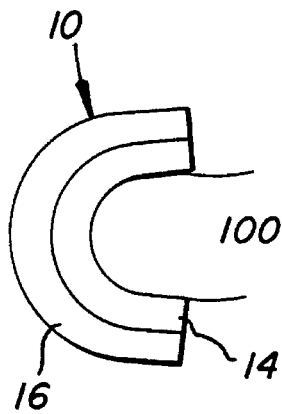
FIG. 2 is a cross sectional view of the displacement sponge of FIG. 1 after the same has been hydrated and expands around an organ.

The preferred embodiment and best mode of the composite tissue displacement invention is shown in FIGS. 1–2. As shown in the drawings, a sterile flexible multi-layer sponge device 10 capable of transmitting force to an organ or tissue 100 is constructed of a multi-layered body 12 of rigid compressed absorbent polyvinyl acetal material. The layered body 12 has two layers of differing density sponge material; a low density sponge material 14 and a high density sponge material 16 which are secured together in one composite piece by ultrasonic welding or a suitable adhesive. The sponge material is produced from polyvinyl acetal (PVAc) polymer by the methods described in U.S. Pat. No. 4,098,728. The sponge material has the desirable medical properties of being highly absorbent to liquids, it is very soft when wet and also has high wet strength. The polyvinyl acetal material has a controlled pore size uniformly distributed throughout the volume of each of the specific layers, the material being fast wicking and having a high liquid holding capacity. The sponge material has immediate wicking and the capacity to absorb water to the extent of up to 25 times its weight in fluids and a retained fluid capacity of 16 times its own weight in fluids as measured by ASTM D-1117-80. Being soft when wet allows the PVAc sponge to conform to the precise space of the cavity or site required for organ protection or to displace or move the organs and/or tissue without damaging same.

The PVAc sponge material is produced by Merocel Corp. located in Mystic, Conn. in a variety of pore or cell sizes. These cell sizes can vary from MEROCEL sponge product designation CF 50 which has a pore size which ranges from about 0.2 mm to about 1.2 mm in diameter; CF 100 which has a pore size which ranges from about 0.02 mm to about 0.6 mm in diameter; CF 150 which has a pore size which ranges from about 0.01 mm to about 0.2 mm in diameter; CF 200 which has a pore size which ranges from about 0.004 mm to about 0.4 mm in diameter; and CF 400 which has a pore size which ranges from about 0.004 mm to about 0.2 mm in diameter as determined by Scanning Electron Microscopy. The aforenoted grade designations CF 50; CF 100; CF 150; CF 200 and CF 400 have a respective average pore size of 0.95 mm; 0.45 mm; 0.35 mm; 0.2 mm (0.21) and 0.2 mm (0.190). The present invention uses the different swelling rates of layered PVAc sponges to achieve a controlled force against organs and tissue.

The inventive sponge composition uses a compound sponge material made of two or more layers of PVAc sponge, one of which is preferably CF 50 as the base low density sponge layer and another greater density or smaller pore size sponge CF number between 150 and 400 as the other layer. The compound sponge has the property of curling or unfolding depending on its shape because of the differences in the material properties of the layers. The various material or layer differentials include (1) the rate of water absorption or wicking; (2) the equilibrium water concentration or fluid capacity; (3) the volumetric expansion upon hydrating dried sponge layers; (4) the volumetric expansion upon hydrating mechanically compressed layers and (5) pretwisting sponge layers or otherwise fixing one relative to the other prior to laminating, adhering, welding or joining. Since the two layers have a different equilibrium level of liquid absorption, it has been found that the curling or folding property is a permanent feature of the wet sponge as long as it remains wet.

Simple mechanical compression serves to decrease the bulk volume of the polyvinyl acetal sponge by lowering the void volume. Upon hydration with any aqueous fluid, the mechanically compressed sponge expands and the original void volume is restored. The extent of volumetric expansion (resultant from hydrating a mechanically compressed sponge layer) increases with increasing void volume of each density of virgin sponge.

There are also additional design options which can be obtained beyond simple mechanical compression. The dry and compressed shape of the device can be designed by selectively compressing all or only a given portion of each sponge layer. Additionally, one or more of the sponge layers can be compressed to impart a delay in the volumetric expansion (normally dependent only on the free wicking rate of each sponge density). This delay results in one layer wicking fluid, hyrating and volumetrically expanding while these dimensional changes have yet to occur in the second layer. Physically this results in the ability to design complex or timed movements and interactions of the composite tissue displacement sponge with the intended tissue site.

Design of composite tissue displacement sponges is also envisioned as part of the invention by incorporating three or more layers, each with specified material properties based upon choices including sponge density, wicking rate, layer-to-layer orientation prior to bonding, as well as the type and extent of mechanical compression.

The layered sponge material is manufactured by layering or stacking two or more differing density sponge materials in layers, cutting and sealing the layers together with an ultrasonic device. The ultrasonic device seals the sponge layers together on their outside edges. If desired the sponge layers can be cut by any standard means and secured together with an adhesive such as Dow 355. The composite sponge material 12 is then compressed and saline or distilled water is applied to the sponge material to swell the material up to expanded size, the same is formed into a desired shape with both ends restrained and then compressed and dried to ambient condition. The sponge material is preferably manufactured so that it is sterile.

This property of differential swelling and curling can be employed in several ways to meet the surgical need for a soft and strong retraction or displacement device.

Such a property in a composite displacement sponge is useful as it allows a displacement sponge to be placed adjacent to a delicate organ such as an ovary, lobe of a parenchymal organ such as the liver or spleen, large or small intestine, or an artery or vein. The sponge will curl and fold, wrapping itself partly around the organ to be protected and swelling to be adjacent and in intimate contact with the specific organ thereby both displacing and protecting it. Alternatively, the invention in its various forms can be used to remove organs from the operative site or position organs into the operative site.

Another application of the differential swelling of a compound layered PVAc sponge 10 is in the case of the requirement to displace tissue or an organ at a specific anatomical location. It is necessary in such an application to fix the device at a specific point within the anatomy. This can be accomplished by a two layer component device where the higher density layer serves as a leg or beam supporting the device against a tissue or bony layer while the other, lower density layer serves as the faster swelling displacing component. Such a device would be useful in applications such as parenchymal organs, an artery or vein, gallbladder or neural tissue displacement.

The compound or bicomponent sponge is also useful for its load bearing properties. A high density layer can serve as a relatively rigid base while a softer, upper layer would apply gentler pressure against the organ minimizing tissue damage. Such a two component layered sponge would be designed to have only minimal curling properties and is useful in displacing large organs or zones of tissues, e.g., omentum or bladder.

Modifications of desired swelling is achieved by using two different thicknesses as well as two different pore sizes of PVAc sponge. It is possible to achieve a wide variety of degrees of curling and folding by the judicious selection of pore size, thickness, layer-to-layer orientation prior to bonding, as well as the type and extent of mechanical compression.

Figure 3:
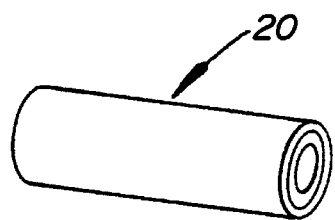
FIG. 3 is a perspective view of an ear pack embodiment of the present invention.
Figure 4:
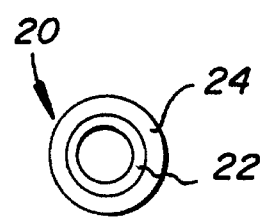
FIG. 4 is an enlarged cross sectional view of the ear pack shown in FIG. 3.

Another embodiment as shown in FIGS. 3 and 4 is an ear pack 20 comprised of two concentric cylinders 22 and 24 in which the inner cylinder 22 is the higher density, smaller pore diameter PVAc sponge such as CF 100, CF 150, CF 200 and CF 400; the outer cylinder 24, completely surrounding the inner sponge is of the lower density, larger pore size sponge such as CF 50. This combination will swell and curl when wetted and follow more closely the irregular curvature of the ear canal.

When a sponge of FIGS. 1–6 is used in endoscopic procedures, the wet sponge in intimate contact with the displaced organ will also protect that organ from becoming dessicated from the non-humidified $CO_2$ gas used to distend the anatomical cavity being treated.

Figure 5:
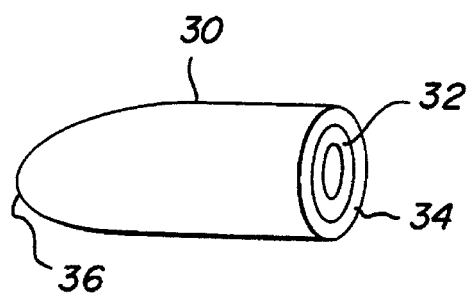
FIG. 5 is a perspective view of an elbow or pouch embodiment of the invention.
Figure 6:
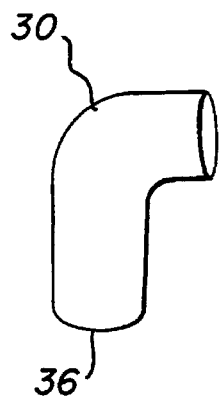
FIG. 6 is a perspective view of the pouch embodiment of FIG. 5 after the same has been hydrated.

An actual pouch 30 such as that shown in FIGS. 5 and 6 can be made from the sponge material with a high density layer 32 and a low density layer 34 to entirely surround the organ being protected. The sponge can be easily removed from the surgical site by compressing the sponge and retrieving it through a trocar portal. The pouch 30 is made from a layered tube having end 36 sealed or closed shut.

Another embodiment of the sterile tissue or organ displacing device is shown in FIGS. 7–9 in the form of a two component disc spacer sponge device 40. The sponge device 40 in its compressed form is in the shape of two separated disc members 42 and 44 connected by bar 46. The bar 46 is constructed of high density CF 150, CF 200 or CF 400 sponge material and each disc member 42 and 44 is constructed of low density CF 50 material. While bar 46 can be constructed of intermediate density CF 100, use of the other high density sponge materials allows greater expansion. The disc members are mounted on each end of bar 46. The device is placed in the appropriate anatomical position and wetted with water or saline. The sponge expands to its full dimension and applies a force along the central axis or bar 46 of the device to each disc thereby displacing the target tissue or organ. Because the PVAc sponge of the low density disc adjacent to the tissue is wet and therefore very soft, the tissue or organ being displaced would be exposed to little trauma.

The disc spacer sponge device 40 is placed between two organs or tissue to separate the same. This density differential allows differential swelling providing a controlled force on an organ or tissue to obtain organ or tissue displacement. FIG. 9 shows the use of the disc spacer device 40 to displace and protect an ovary 102 and fallopian tube 103 during surgery by placing disc 42 on the vagina 104 and disc 44 against the ovary 102 to move the ovary 102 away from the surgical area during surgery on the cervix 106 or uterus 108. Positioning is maintained by bracing the organ/device against the abdominal wall, peritoneal surface of the uterus, or other firm pelvic structure.

In the foregoing description, the invention has been described with reference to a particular preferred embodiment, although it is to be understood that specific details shown are merely illustrative, and the invention may be carried out in other ways without departing from the true spirit and scope of the following claims:

What is claimed:

1. A sterile medical sponge device comprising a rigid dry absorbent compressed sponge body constructed of at least two plates of sponge material, each plate being secured to the other plate and having a different density, said sponge body forming a curved configuration when hydrated.

2. A medical sponge device as claimed in claim 1 wherein one of said plates has a pore size ranging from about 0.2 mm to about 1.2 mm and the other plate has a pore size ranging from about 0.01 mm to about 0.2 mm.

3. A medical sponge device as claimed in claim 1 wherein one of said plates has a pore size ranging from about 0.2 mm to about 1.2 mm and the other plate has a pore size ranging from 0.004 mm to about 0.4 mm.

4. A medical sponge device as claimed in claim 1 wherein one of said plates has a pore size ranging from about 0.2 mm to about 1.2 mm and the other plate has a pore size ranging from about 0.02 mm to about 0.6 mm.

5. A medical sponge device as claimed in claim 1 wherein each plate is constructed of polyvinyl acetal of different average pore size densities.

6. A medical sponge device as claimed in claim 1 wherein said sponge plates are secured together by ultrasonic welding.

7. A medical sponge device as claimed in claim 1 wherein said sponge plates are secured together by adhesive.

8. A medical ear pack sponge comprising a cylindrical rigid dry absorbent shaped sponge body constructed of a plurality of concentric layers of sponge material, each of said layers being secured together and having different average pore size densities, said sponge body when placed in an ear canal and hydrated, expanding and curling to follow closely the curvature of the ear canal.

9. A medical ear pack sponge as claimed in claim 8 wherein said plurality of concentric layers of sponge material are two layers of polyvinyl acetal of differing densities.

10. A medical ear pack sponge as claimed in claim 9 wherein an inner cylinder layer of the two layers of polyvinyl acetal is of a higher pore density than an outer cylinder layer.

11. A medical ear pack sponge as claimed in claim 10 wherein said outer cylinder layer has a pore size ranging from about 0.2 mm to about 1.2 mm and the inner cylinder layer has a pore size ranging from about 0.01 mm to about 0.5 mm.

12. A medical ear pack sponge as claimed in claim 10 wherein said outer cylinder layer has a pore size ranging from about 0.2 mm to about 1.2 mm and the inner cylinder layer has a pore size ranging from about 0.004 mm to about 0.2 mm.

13. A medical ear pack sponge as claimed in claim 10 wherein said outer cylinder layer has a pore size ranging from about 0.2 mm to about 1.2 mm and the inner cylinder layer has a pore size ranging from about 0.02 mm to about 0.6 mm.

14. A medical ear pack sponge as claimed in claim 10 wherein said outer cylinder layer has a pore size ranging from about 0.2 mm to about 1.2 mm and the inner cylinder layer has a pore size ranging from about 0.004 mm to about 0.4 mm.

15. A sterile medical organ pouch comprising a tubular rigid dry absorbent shaped sponge body constructed of a plurality of adjacent layers of sponge material defining an interior chamber of a size adapted to receive a predetermined organ, one end of said tubular body being closed, each of said layers having different pore size densities from one of the other layers, said sponge body when hydrated, curling to move an organ placed therein.

16. A medical organ pouch as claimed in claim 15 wherein said plurality of adjacent layers of sponge material are two layers of polyvinyl acetal of differing densities.

17. A medical organ pouch as claimed in claim 16 wherein an inner layer of the two layers of polyvinyl acetal is of a higher density than an outer layer.

18. A medical organ pouch as claimed in claim 16 wherein said outer layer has a pore size ranging from about 0.2 mm to about 1.2 mm and the inner layer has a pore size ranging from about 0.02 mm to about 0.6 mm.

19. A medical organ pouch as claimed in claim 16 wherein said outer layer has a pore size ranging from about 0.2 mm to about 1.2 mm and the inner layer has a pore size ranging from about 0.01 mm to about 0.5 mm.

20. A medical organ pouch as claimed in claim 16 wherein said outer layer has a pore size ranging from about 0.2 mm to about 1.2 mm and the inner layer has a pore size ranging from about 0.004 mm to about 0.4 mm.

21. A medical organ pouch as claimed in claim 16 wherein said outer layer has a pore size ranging from about 0.2 mm to about 1.2 mm and the inner layer has a pore size ranging from about 0.004 mm to about 0.2 mm.

22. An organ displacement device comprising a tubular rigid bar member and a disc shaped member secured to each end of said bar member, said bar member and disc shaped members being formed of dry absorbent compressed sponge material, said bar member being constructed of a sponge material having a known pore size density and each of said disc shaped members being constructed of a organ displacement material of a pore size of lesser density, said organ displacement device bar member and disc shaped members when hydrated expanding axially for movement of an organ placed against one of said disc shaped members.

23. An organ displacement device as claimed in claim 22 wherein said sponge material is sterile polyvinyl acetal of differing densities.

24. An organ displacement device as claimed in claim 22 wherein said disc shaped members have a pore size ranging from about 0.2 mm to about 1.2 mm and the connecting bar member has a pore size ranging from about 0.02 mm to about 0.6 mm.

25. An organ displacement device as claimed in claim 22 wherein said disc shaped members have a pore size ranging from about 0.2 mm to about 1.2 mm and the connecting bar member has a pore size ranging from about 0.004 mm to about 0.2 mm.

26. An organ displacement device as claimed in claim 22 wherein said disc shaped members have a pore size ranging from about 0.2 mm to about 1.2 mm and the connecting bar member has a pore size ranging from about 0.01 mm to about 0.5 mm.

27. An organ displacement device as claimed in claim 22 wherein said disc shaped members have a pore size ranging from about 0.2 mm to about 1.2 mm and the connecting bar member has a pore size ranging from about 0.004 mm to about 0.4 mm.

\* \* \* \* \*